US011872224B2

(12) United States Patent
Yen et al.

(10) Patent No.: US 11,872,224 B2
(45) Date of Patent: Jan. 16, 2024

(54) AMORPHOUS SOLID DISPERSION FORMULATION

(71) Applicants: TaiGen Biotechnology Co., Ltd., Taipei (TW); TaiGen Biopharmaceuticals Co. (Beijing), Ltd., Beijing (CN)

(72) Inventors: Chi-Feng Yen, Taipei (TW); Fang-Wei Tien, Taipei (TW)

(73) Assignees: TaiGen Biotechnology Co., Ltd., Taipei (TW); TaiGen Biopharmaceuticals Co. (Beijing), Ltd., Beijing (CN)

( * ) Notice: Subject to any disclaimer, the term of this patent is extended or adjusted under 35 U.S.C. 154(b) by 0 days.

(21) Appl. No.: 17/564,418

(22) Filed: Dec. 29, 2021

(65) Prior Publication Data

US 2022/0202817 A1 Jun. 30, 2022

Related U.S. Application Data

(60) Provisional application No. 63/131,886, filed on Dec. 30, 2020.

(51) Int. Cl.
*A61K 31/495* (2006.01)
*A61K 31/5025* (2006.01)
*A61K 47/10* (2017.01)
*A61K 47/32* (2006.01)
*A61K 47/38* (2006.01)

(52) U.S. Cl.
CPC .......... *A61K 31/5025* (2013.01); *A61K 47/10* (2013.01); *A61K 47/32* (2013.01); *A61K 47/38* (2013.01)

(58) Field of Classification Search
CPC .................................................. A61K 31/495
See application file for complete search history.

(56) References Cited

U.S. PATENT DOCUMENTS 10,596,171 B2 * 3/2020 Lin .................... A61K 31/5025

FOREIGN PATENT DOCUMENTS

WO WO-2019144089 A1 * 7/2019 ......... A61K 31/5025

OTHER PUBLICATIONS

BASF. "Soluplus®". Product Information Sheet. (Oct. 6, 2018). Accessed Jun. 29, 2023. Available from: < https://www.pharmaexcipients.com/wp-content/uploads/attachments/BASF_Soluplus_Onepager.pdf?t=1532108514 >. (Year: 2018).*
Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*

* cited by examiner

Primary Examiner — John S Kenyon
(74) Attorney, Agent, or Firm — McCarter & English, LLP; Yu Lu

(57) ABSTRACT

The present disclosure provides an amorphous solid dispersion containing a Cap-dependent endonuclease inhibitor or a pharmaceutically acceptable salt thereof for oral administration, wherein the Cap-dependent endonuclease inhibitor or a pharmaceutically acceptable salt thereof is dispersed in a matrix formed from the pharmaceutically acceptable polymer. Further disclosed are methods for preparing a above amorphous solid dispersion and a use thereof for treating virus infection and a pharmaceutical composition containing same.

16 Claims, No Drawings

AMORPHOUS SOLID DISPERSION FORMULATION

REFERENCE TO RELATED APPLICATION

This application claims the benefit of the filing date under 35 U.S.C. 119(e) to U.S. Provisional Patent Application No. 63/131,886, filed on Dec. 30, 2020, the entire contents of which are incorporated herein by reference.

TECHNICAL FIELD

The present disclosure relates to an amorphous solid dispersion (ASD) containing anti-influenza compounds, and methods for preparing the same. In addition, the present disclosure relates to a pharmaceutical composition containing above amorphous solid dispersion (ASD), and a use thereof in treating influenza virus infection.

BACKGROUND OF THE INVENTION

Cap-dependent endonuclease is an essential enzyme in the mRNA synthesis of influenza viruses. Inhibitors of viral Cap-dependent endonuclease are found to be effective against both influenza virus A and B. Several compounds displayed potent antiviral activity against influenza virus by inhibiting the activity of Cap-dependent endonuclease. In PCT published application, WO2019/144089, novel heterocyclic compounds as potent Cap-dependent endonuclease inhibitors were first disclosed. However, one of the major limitations associated with these heterocyclic compounds are their low aqueous solubility. With the poor solubility, the challenge for the heterocyclic compound is how to develop it as a drug that can be administered orally. Oral administration remains the most desirable dosage form due to its generally lower cost of production, the preference of patients and caregivers and overall higher compliance rates. Therefore, for a new drug substance, it is important to find the suitable oral formulation during developmental phases. The present disclosure relates to the development of the oral solid formulation of the heterocyclic compounds disclosed in WO2019/144089.

SUMMARY OF THE INVENTION

The present disclosure provides an amorphous solid dispersion comprising a Cap-dependent endonuclease inhibitor or a pharmaceutically acceptable salt thereof, or a prodrug thereof for oral administration. In one aspect, a method for preparing same is also provided.

In another aspect, the present disclosure provides an oral pharmaceutical composition comprising an amorphous solid dispersion of a Cap-dependent endonuclease inhibitor or a pharmaceutically acceptable salt thereof, or a prodrug thereof.

In yet another aspect, the present disclosure further provides a method for treating or preventing virus infection/disease (e.g., influenza), comprising administering a therapeutically effective amount of the amorphous solid dispersion or the oral pharmaceutical composition to a subject in need thereof.

DETAILED DESCRIPTION OF THE INVENTION

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

The term "about" means within an acceptable error range for the particular value as determined by persons of ordinary skill in the art, which will depend in part on how the value is measured or determined, i.e., the limitations of the measurement system. As used herein, when referring to a measurable or calculated value such as an amount, a temporal duration, a concentration, a ratio, and the like, may encompass variations of ±20%, ±10%, ±5%, ±1%, or ±0.1% from the specified value, as such variations are appropriate to perform the disclosed methods.

The terms "treat," "treating," and "treatment" used herein are meant to include alleviating or eliminating a disorder, disease, or condition, or one or more of the symptoms associated with the disorder, disease, or condition; or alleviating or eradicating the cause(s) of the disorder, disease, or condition itself.

The terms "prevent," "preventing," and "prevention" used herein are meant to include a method of delaying and/or eliminating the onset of a disorder, disease, or condition, and/or its attendant symptoms; avoiding a subject from acquiring a disorder, disease, or condition; or reducing a subject's risk of acquiring a disorder, disease, or condition.

The terms "patient," "individual" or "subject" used herein refer to a human or a non-human mammal. The terms "patient," "individual" or "subject" can be used interchangeably in this content. In one embodiment, the patient, individual, or subject is human.

The term "therapeutically effective amount" used herein refers to an amount of an active compound that is sufficient to prevent progression of, or alleviate to some extent, one or more of the symptoms of the disorder, disease, or condition being treated.

The term "pharmaceutically acceptable carrier" used herein refers to a material or vehicle involved in carrying or delivering a compound useful within or to the patient such that it may perform its intended function and does not eliminate the biological activity of the administered compound. In one embodiment, the pharmaceutically acceptable carrier is a polymer.

The term "one or more" or "single or multiple" used herein refers to either one or a number above one (e.g., 2, 3, 4, 5, 6, 7 or above). The term "one or more" or "single or multiple" can be used interchangeably in this content.

The term "halogen" used herein refers to fluorine, chlorine, bromine or iodine.

The term "$C_{1-4}$ alkyl" or "$C_{1-8}$ alkyl" used herein refers to a straight- or branched-chain saturated hydrocarbon group containing 1 to 4 (e.g., 1 to 2 and 1 to 3), or 1 to 8 (e.g., 1 to 3, 1 to 4, 1 to 5, 1 to 6 and 1 to 7) carbon atoms. Examples of alkyl include methyl, ethyl, n-propyl, isopropyl, n-butyl, isobutyl, sec-butyl, tert-butyl, pentyl, hexyl, heptyl, octyl, and the like.

The term "$C_{1-4}$ alkoxy" used herein refers to the group —$OR^a$, wherein $R^a$ is a $C_{1-4}$ alkyl. Examples of $C_{1-4}$ alkoxy include methoxy, ethoxy, n-propoxy, isopropoxy, n-butoxy, iso-butoxy, sec-butoxy, tert-butoxy, and the like.

The term "$C_{1-4}$ alkylamino" used herein refers to the group —$NHR^b$, wherein $R^b$ is a $C_{1-4}$ alkyl. Examples of $C_{1-4}$ alkylamino include methylamino, ethylamino, isopropylamino, and the like.

The term "carbocycle" used herein refers to a 3- to 16-membered cyclic hydrocarbon group and includes aromatic carbocycle and non-aromatic carbocycle.

The term "aromatic carbocycle" used herein refers to a cyclic aromatic hydrocarbon group which is a monocycle or a polycycle having two or more rings. Examples include benzene, naphthalene, andanthracene.

The term "non-aromatic carbocycle" used herein refers to saturated carbocycle or unsaturated non-aromatic carbocycle which is monocyclic or which is constituted of two or more rings. A "non-aromatic carbocycle" constituted of two or more rings includes a fused cyclic group wherein a non-aromatic monocyclic carbocycle or a non-aromatic carbocycle constituted of two or more rings is fused with a ring of the above "aromatic carbocycle". In addition, the "non-aromatic carbocycle" constituted of two or more rings also includes bridged ring system, and spiro ring system.

The term "heterocycle" used herein includes an aromatic heterocycle and a non-aromatic heterocycle.

The term "aromatic heterocycle" used herein refers to an aromatic ring which is monocyclic, or which constitutes of two or more rings, containing one or more heteroatom(s) selected independently from O, S and N. An "aromatic heterocyclyl" of two or more rings includes a fused cyclic group wherein aromatic monocyclic heterocyclyl or aromatic heterocyclyl consisting of two or more rings is fused with a ring of the above "aromatic carbocyclyl".

The term "non-aromatic heterocycle" used herein refers to a non-aromatic ring which is monocyclic, or which constitutes of two or more rings, containing one or more heteroatom(s) selected independently from O, S and N. A "non-aromatic heterocycle" constitutes of two or more rings includes a fused cyclic group wherein non-aromatic monocyclic heterocycle or non-aromatic heterocycle constituting of two or more ring(s) is fused with a ring of the above "aromatic carbocycle", "non-aromatic carbocycle" and/or "aromatic heterocycle". In addition, the "non-aromatic heterocycle" constitutes of two or more rings also includes bridged ring system, and spiro ring system.

The term "pharmaceutically acceptable salt" used herein refers to the salts of the compound of the present disclosure that are suitable for use in contact for the tissue of humans and lower animals without any inappropriate toxicity, irritation, allergic response and the like within a reliable medical evaluation range reaction. It includes pharmaceutically acceptable acid additive salts and base addititve salts, which can be effectively used as specific purpose and compatible with compounds described herein. The pharmaceutically acceptable salts are reviewed in S. M. Birge et al., *J. Pharm. Sci.*, 1977, 66, 1-19.

The term "prodrug" used herein refers to a bioreversible derivative of a drug molecule that undergoes an enzymatic and/or chemical transformation to release the active parent drug, which can then exert the desired pharmacological effect. For example, the compounds used herein may form prodrugs at hydroxyl functionalities using ester, amide, carbonate, carbonyl, carbamate, etc., groups as the prodrug forming moieties.

The term "amorphous" used herein refers to a solid form of a molecule and/or ion that is not crystalline. An amorphous solid dose not display a definite X-ray diffraction pattern with sharp maxima.

The term "solid dispersion" used herein refers to a molecular dispersion of a compound, particularly a drug substance within a pharmaceutically acceptable carrier (such as polymer). The term solid dispersion in general means a system in solid state comprising at least two components, wherein one component is dispersed substantially evenly throughout the other component(s). For example, solid dispersions may be the dispersion of one or more active ingredients in an inert carrier or matrix at solid state, prepared by the spray drying, hot melt extrusion, fluid bed, or lyophilization methods and the like. Formation of a solid dispersion may provide a means of reducing the particle size to nearly molecular levels.

As used herein, a polyvinylpyrrolidone (also called PVP) refers to a high molecular compound obtained by polymerizing N-vinyl-2-pyrrolidone. Examples of the polyvinylpyrrolidone include PVP-K17, PVP-K25, PVP-K30, PVP-K40, PVP-K50, PVP-K60, PVP-K70, PVP-K80, PVP-K85, PVP-K90, PVP-K120, and the like.

As used herein, a polyvinylpyrrolidone/vinyl acetate copolymer (also called PVP-VA) refers to the copolymer of vinyl pyrrolidone (VP) and vinyl acetate (VA) monomers. Examples of the polyvinylpyrrolidone/vinyl acetate copolymer include PVP-VA64, and the like.

As used herein, a methacrylic acid and methyl methacrylate copolymer refers to a copolymer derived from esters of acrylic acid and methacrylic acid. Eudragit® is the brand name for a diverse range of the copolymers of methacrylic acid and methyl methacrylate. Examples of the copolymers of methacrylic acid and methyl methacrylate copolymer include Eudragit® EPO, Eudragit® E100, Eudragit® RS100, Eudragit® RL100, Eudragit® L100, Eudragit® NE, Eudragit® NM, Eudragit® FS, and the like.

As used herein, a polyethylene glycol (also called PEG) refers to a polymer containing ethylene glycol monomer units of formula $-O-CH_2-CH_2-$. Examples of the polyethylene glycol include PEG1000, PEG1500, PEG2000, PEG2500, PEG3000, PEG3350, PEG3500, PEG4000, PEG5000, PEG6000, PEG8000, and the like.

As used herein, a polyoxyethylene-polyoxypropylene copolymer refers to a copolymer that has both oxyethylene monomer units and oxypropylene monomer units. Suitable polyoxyethylene-polyoxypropylene copolymers can be of any chain length or molecular weight, and can include branching. The chain ends may have free hydroxyl groups or may have one or more hydroxyl groups etherified with lower alkyl or carboxyl group. The polyoxyethylene-polyoxypropylene copolymers can also include other monomers which are copolymerized and which form part of the backbone. In some embodiments, the polyoxyethylene-polyoxypropylene copolymer are commercially available form BASF Performance Chemicals under the trade name Pluronic®, and which comprises the group of surfactants designated by the CTFA name of Poloxamer 108, 124, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403.

As used herein, a hydroxypropyl cellulose is also called HPC. Examples of the hydroxypropyl cellulose include HPC-SSL, HPC-SL, HPC-L, HPC-M, HPC-H, and the like, according to their average molecular weights.

As used herein, a hydroxypropyl methyl cellulose is also called HPMC. Examples of the hydroxypropyl methyl cellulose include HPMC E3, HPMC E5, HPMC E6, HPMC E16, HPMC E30, HPMC E50, HPMC E50Lv, and the like, according to their viscosities.

As used herein, a hydroxypropyl methyl cellulose acetate succinate (also called HPMCAS) refers to a mixture of acetic acid and monosuccinic acid esters of hydroxypropylmethyl cellulose. In one embodiment, the HPMCAS comprises various types, such as HPMCAS-LF, HPMCAS-LG, HPMCAS-MF, HPMCAS-MG, HPMCAS-HF, HPMCAS-HG, and the like.

As used herein, a hydroxypropyl methyl cellulose phthalate is also called HPMCP. Examples of HPMCP include HPMCP HP-50, HPMCP HP-55, HPMCP HP-55S, and the like.

In one aspect, the present disclosure provids an amorphous solid dispersion comprising a Cap-dependent endonuclease inhibitor for oral administration, wherein the Cap-dependent endonuclease inhibitor is represented by Formula (I) or a pharmaceutically acceptable salt thereof:

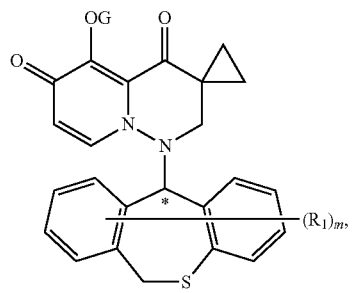
(I)

wherein

G is hydrogen or a prodrug group;

$R_1$ is halogen, deuterium, or $C_{1-4}$ alkyl;

m is an integer of 1 to 9; and the star (*) indicates a chiral center.

In one embodiment, $R_1$ is halogen, deuterium, or methyl. In another embodiment, $R_1$ is halogen or deuterium. In yet another embodiment, $R_1$ is fluorine or deuterium.

In one embodiment, the cyclic group in Formula (I) represented by the formula:

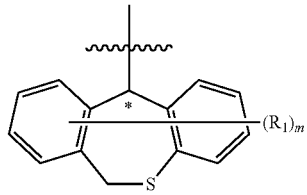

is a cyclic group represented by any one of the following structures:

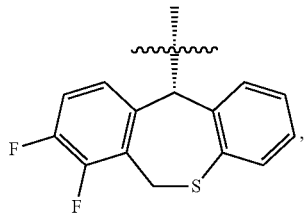

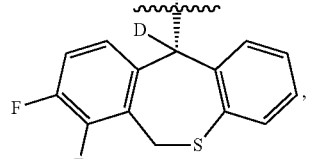,

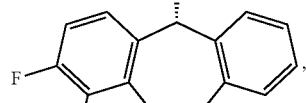,

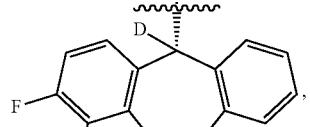,

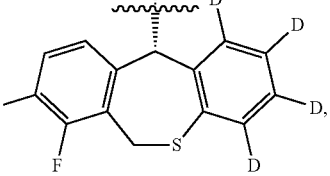,

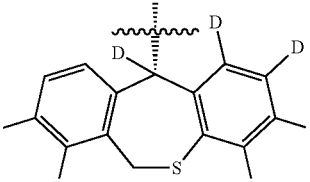,

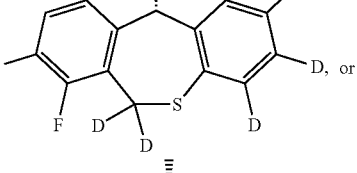, or

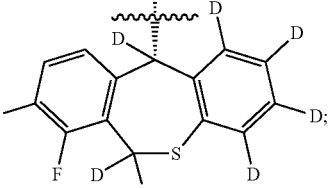;

G is hydrogen or —C($R_2R_2'$)—O—C(=O)—O—$R_3$; each of $R_2$ and $R_2'$, independently, is hydrogen or $C_{1-4}$ alkyl; and $R_3$ is $C_{1-4}$ alkyl.

In one embodiment, m is 1, 2, 3, 4, 5, 6, 7, 8, or 9. In one embodiment, G is selected from the group consisting of hydrogen, —C(R$_2$R$_2$')—O—C(=O)—R$_3$, —C(R$_2$R$_2$')—O—C(=O)—O—R$_3$, —C(R$_2$R$_2$')—O—C('O)—C(R$_2$R$_2$')—NR$_4$—C(=O)—O—C(R$_2$R$_2$')—R$_3$', —C(R$_2$R$_2$')—C(R$_2$R$_2$')—O—C(=O)—R$_3$, —C(R$_2$R$_2$')—R$_3$', —C(=O)—R$_3$, —C(=O)—NR$_3$R$_4$, and

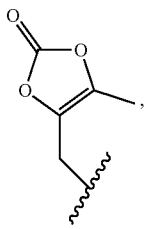 [SMILES: *Cc1oc(=O)oc1C]

in which each of R$_2$, R$_2$', and R$_4$, independently, is hydrogen or C$_{1-8}$ alkyl; each of R$_3$, and R$_3$', independently, is C$_{1-8}$ alkyl, C$_{3-10}$ carbocyclyl, or C$_{3-10}$ heterocyclyl. In another embodiment, G is selected from hydrogen, —C(R$_2$R$_2$')—O—C(=O)—R$_3$, —C(R$_2$R$_2$')—O—C(=O)—O—R$_3$, —C(R$_2$R$_2$')—R$_3$', —C(=O)—R$_3$, and —C(=O)—NR$_3$R$_4$. In still another embodiment, G is hydrogen, or —C(R$_2$R$_2$')—O—C(=O)—O—R$_3$.

In one embodiment, each of R$_2$, R$_2$', and R$_4$, independently, is hydrogen or C$_{1-4}$ alkyl. In another emdobiment, each of R$_2$, R$_2$', and R$_4$, independently, is hydrogen, methyl, ethyl, propyl, or isopropyl.

In one embodiment, R$_3$ is C$_{1-4}$ alkyl. In another embodiment, R$_3$ is methyl, ethyl, propyl, or heptyl.

In one embodiment, R$_3$' is C$_{3-10}$ carbocyclyl. In another embodiment, R$_3$' is aryl. In yet another embodiment, R$_3$' is phenyl.

In one embodiment, G is selected from the group consisting of hydrogen,

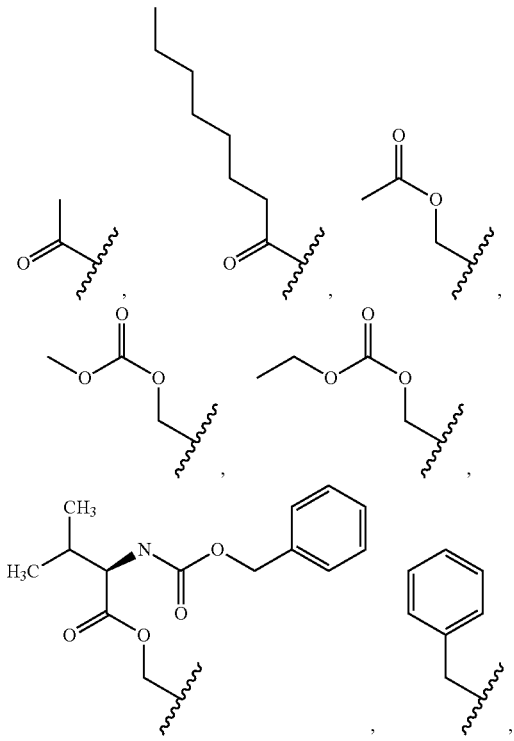

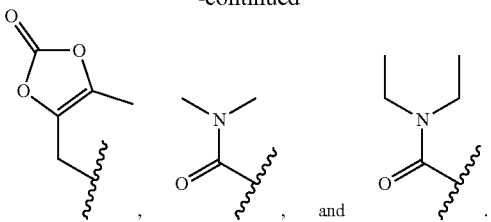

In one embodiment, the compound of Formula (I) is 1'-((11S)-7, 8-difluoro-6H,11H-dibenzo[b,e]thiepin-11-yl)-1',2'-dihydro-5'-hydroxy-spiro [cyclopropane-1,3'-(3H) pyrido[1,2-b]pyridazine-4',6'-dione or a pharmaceutically acceptable salt thereof.

In one embodiment, the compound of Formula (I) is [1-((11S)-7 8-difluoro(6H,11H-dibenzo[c,f]thiepin-11-yl))-4,6-dioxospiro[1,2,3,9-tetrahydropyridino[1,2-e] pyridazine-3,1'-cyclopropane]-5-yloxy]methyl methoxyformate or a pharmaceutically acceptable salt thereof.

In some embodiments, the compounds of the present disclosure can be prepared according to the methods/procedures disclosed in PCT published application No. WO2019/144089, or No. WO2021/239126, which is incorporated herein by reference in its entirety.

In one embodiment, the present disclosure provides an amorphous solid dispersion of a compound of Formula (I) or a pharmaceutically acceptable salt thereof, further comprising a pharmaceutically acceptable polymer.

In another embodiment, disclosed herein is an amorphous solid dispersion comprising a compound of Formula (I) or a pharmaceutically acceptable salt thereof, and a pharmaceutically acceptable polymer, wherein the compound of Formula (I) or the pharmaceutically acceptable salt thereof, is dispersed within a polymer matrix formed by the pharmaceutically acceptable polymer in its solid state.

The pharmaceutically acceptable polymer used in the amorphous solid dispersion of the present disclosure is a water-soluble polymer. The suitable water-soluble polymer should act as a water-soluble carrier to make the active ingredient hydrophilic, thereby improving its solubility, and it also helps maintaining the solid dispersions in an amorphous state. Some common examples of the water-soluble polymer include but not limited to vinyl polymers and copolymers, polyvinyl pyrrolidone (PVP), polyvinylpyrrolidone/vinyl acetate copolymer (PVP-VA), polyvinyl alcohols (PVA), polyvinyl alcohol polyvinyl acetate copolymers, polyethylene polyvinyl alcohol copolymers, polyvinyl caprolactam and polyvinyl acetate, polyvinyl caprolactam-polyvinyl acetate-polyethylene glycol graft copolymer (also referred to as Soluplus), acrylate and methacrylate copolymers, methacrylic acid and methyl methacrylate copolymer (such as Eudragit), polyethylene glycol (PEG), polyoxyethylene-polyoxypropylene copolymers (also referred to as poloxamers), cellulose derivatives, hydroxypropyl methyl cellulose acetate (HPMCA), hydroxypropyl methyl cellulose (HPMC), hydroxypropyl cellulose (HPC), methyl cellulose, hydroxyethyl methyl cellulose, hydroxyethyl cellulose, hydroxyethyl cellulose acetate, hydroxyethyl ethyl cellulose, hydroxypropyl methyl cellulose acetate succinate (HPMCAS), hydroxypropyl methyl cellulose phthalate (HPMCP), Kollidon SR (polyvinyl acetate 80% and polyvinyl pyrrolidone 20%), carboxymethylethyl cellulose (CMEC), cellulose acetate phthalate (CAP), cellulose acetate succinate (CAS), hydroxypropyl methyl cellulose acetate phthalate (HPMCAP), cellulose acetate trimellitate (CAT), hydroxypropyl methyl cellulose acetate trimellitate (HPMCAT), carboxymethylcellulose acetate butyrate (CM-CAB), or combinations thereof.

In one embodiment, the pharmaceutically acceptable polymer is polyvinylpyrrolidone/vinyl acetate (PVP-VA), polyvinyl caprolactam-polyvinyl acetate-polyethylene glycol graft copolymer (Soluplus), methacrylic acid and methyl methacrylate copolymer, hydroxypropyl cellulose (HPC), hydroxypropyl methyl cellulose acetate succinate (HPMCAS), hydroxypropyl methyl cellulose phthalate (HPMCP), Polyethylene glycol (PEG), or Kollidon SR. In another embodiment, the polyvinylpyrrolidone/vinyl acetate copolymer is PVP-VA64, the HPC is HPC-SSL, the HPMCAS is HPMCAS-MG or HPMCAS-HG, the HPMCP is HPMCP HP-55, the PEG is PEG3350, and the copolymer of methacrylic acid and methyl methacrylate is Eudragit® EPO.

In one embodiment, the pharmaceutically acceptable polymer is polyvinyl caprolactam-polyvinyl acetate-polyethylene glycol graft copolymer, hydroxypropyl cellulose (HPC), or hydroxypropyl methyl cellulose acetate succinate (HPMCAS). In another embodiment, the pharmaceutically acceptable polymer is polyvinyl caprolactam-polyvinyl acetate-polyethylene glycol graft copolymer, HPC-SSL, HPMCAS-MG, or HPMCAS-FIG. In yet another embodiment, the pharmaceutically acceptable polymer is polyvinyl caprolactam-polyvinyl acetate-polyethylene glycol graft copolymer, or HPC-SSL.

In one embodiment, the pharmaceutically acceptable polymer is polyvinyl caprolactam-polyvinyl acetate-polyethylene glycol graft copolymer. In another embodiment, the pharmaceutically acceptable polymer is HPC-SSL.

In one embodiment, disclosed herein is an amorphous solid dispersion comprising a compound of Formula (I) or a pharmaceutically acceptable salt thereof and a pharmaceutically acceptable polymer, wherein the weight ratio of the compound of Formula (I) or a pharmaceutically acceptable salt thereof to the pharmaceutically acceptable polymer is about 4:1, 3.5:1, 3:1, 2:5:1, 2:1, 1.5:1, 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, or 1:10. In another embodiment, the weight ratio of the compound of Formula (I) or a pharmaceutically acceptable salt thereof to the pharmaceutically acceptable polymer is in the range between any two ratios mentioned above, for example, 2:1 to 1:7, 1:1 to 1:7, 1:1 to 1:6.5, 1:1 to 1:6, 1:1 to 1:5.5, 1:1 to 1:5, 1:1 to 1:4.5, 1:1 to 1:4, 1:1 to 1:3.5,1:1 to 1:3, 1:1 to 1:2.5, 1:1 to 1:2, 1:1.5 to 1:7, 1:1.5 to 1: 6.5, 1:1.5 to 1:6, 1:1.5 to 1:5.5, 1:1.5 to 1:5, 1:1.5 to 1: 4.5, 1:1.5 to 1:4, 1:1.5 to 1:3.5, 1:1.5 to 1:3, 1:2 to 1:5, 1:2 to 1:4, or 1:2 to 1:3.

In one embodiment, the amount of the compound of Formula (I) or a pharmaceutically acceptable salt thereof in the amorphous solid dispersion is in general 10-60%, 10-55%, 10-50%, 10-45%, 10-40%, 15-60%, 15-55%, 15-50%, 15-45%, or 15-40% by weight. For example, the amount of the compound of Formula (I) or a pharmaceutically acceptable salt thereof in amorphous solid dispersion (drug loading) is about 15%, 25%, 33%, 40% or 50% by weight. In one embodiment, the amorphous solid dispersion of the compound of Formula (I) or a pharmaceutically acceptable salt thereof comprises 10-60% w/w (percentage by weight) of the compound of Formula (I) or a pharmaceutically acceptable salt thereof and 40-90% w/w (percentage by weight) of the pharmaceutically acceptable polymer. In another embodiment, the amorphous solid dispersion of the compound of Formula (I) or a pharmaceutically acceptable salt thereof comprises 15-50% w/w (percentage by weight) of the compound of Formula (I) or a pharmaceutically acceptable salt thereof and 50-85% w/w (percentage by weight) of the pharmaceutically acceptable polymer.

In another aspect, the amorphous solid dispersion described herein can be administered orally to a subject (e.g., a human) in need thereof to treat or prevent the infectious diseases such as influenza.

In one embodiment, the amorphous solid dispersion of the present disclosure may be prepared by methods well known in the art, such as spray drying, hot melt extrusion, fluid bed, or lyophilization technique. In one embodiment, the amorphous solid dispersion is prepared by spray drying technique.

In one embodiment, the amorphous solid dispersion of the present disclosure is prepared by dissolving a compound of Formula (I) or a pharmaceutically acceptable salt thereof in a sufficient amount of an organic solvent, and mixing the resultant solution with a solution containing a pharmaceutically acceptable polymer. Therefore a spray solution is obtained. The solvent may then be evaporated away, leaving the drug dispersed/dissolved in the matrix. Any organic solvent that can dissolve or disperse a compound of Formula (I) or a pharmaceutically acceptable salt thereof and the pharmaceutical acceptable polymer described above can be used. Examples of the organic solvent include lower carbon-number alcohols (e.g., methanol, ethanol, propanol, or isopropanol), ketone (e.g., acetone, methyl ethyl ketone or methyl isobutyl ketone), haloalkane (e.g., dichloromethane, chloroform or carbon tetrachloride), acetic acid, ethyl acetate, N,N-dimethylformamide, DMSO, tetrahydrofuran, or a mixture thereof.

In one embodiment, the preparation of the amorphous solid dispersion comprises following steps of: (i) dissolving a compound of Formula (I) or a pharmaceutically acceptable salt thereof and a pharmaceutically acceptable polymer in a solvent, and (ii) drying the solution obtained in step (i).

In one embodiment, step (i) comprises: dissolving a compound of Formula (I) or a pharmaceutically acceptable salt thereof in a sufficient amount of an organic solvent; dissolving a pharmaceutically acceptable polymer in a solvent; and mixing the two solutions.

In one embodiment, step (ii) comprises spray drying. In another embodiment, step (ii) comprises spray drying in combination with a fluid bed. In a further embodiment, step (ii) comprises evaporation of the solvent using a rotary evaporator.

The term "spray drying" is used conventionally and broadly refers to processes involving breaking up liquid mixtures into small droplets (atomization) and rapidly removing solvent from the mixture in a spray-drying apparatus (e.g., a nozzle) where there is a strong driving force for evaporation of solvent from the droplets. In a typical spray drying process, the feed liquid may be a solution, slurry, emulsion, gel or paste, provided it is capable of being delivered by pump and being atomized.

The properties of the amorphous solid dispersion of the present disclosure can be characterized by polarized light microscopy (PLM), X-ray powder diffraction (XRPD), thermogravimetric analysis (TGA) and particle size distribution (PSD). The thermochemical property of the amorphous solid dispersion is analyzed with a differential scanning calorimeter (DSC). The results show that the amorphous solid dispersion of the compound of Formula (I) or a pharmaceutically acceptable salt thereof only has one glass transition temperature and does not show any endothermic peak (melting peak), which confirms that the compound of Formula (I) or a pharmaceutically acceptable salt thereof is amorphous in the amorphous solid dispersion. The resulting amorphous solid dispersion can be formulated into pharmaceutical compositions that exhibit high bioavailability.

In another aspect, the present disclosure is also directed to a pharmaceutical composition comprising a therapeutically effective amount of a compound of Formula (I) or a pharmaceutically acceptable salt thereof in amorphous solid dispersion form. In one embodiment, the pharmaceutical compositions comprising the amorphous solid dispersion of the present disclosure are oral or inhalation formulations in the form of capsules, tablets, powders, pellets, pills, suspensions, granules, or inhalants. The form of the pharmaceutical composition used may be coated, for example using an enteric coating. The pharmaceutical compositions can be administered in either single or multiple doses via oral or inhalation administration.

In one embodiment, a pharmaceutical composition comprises an amorphous solid dispersion of the present disclosure and optionally one or more pharmaceutically acceptable excipients that have no bioactivity and no reaction with the active compound. Examples of pharmaceutically acceptable excipients include binders, glidants, plasticizers, solubilizers, stabilizing agents, antioxidants, diluents, surfactants, disintegrants, lubrients, fillers, wetting agents, sweeteners, colorants, flavors, or mixtures thereof. In some embodiments, when the composition is a powder, the pharmaceutical acceptable excipient is a finely divided solid in a mixture with the finely divided active component. In some embodiments, when the composition is formulated into a tablet, the active component (i.e. amorphous solid dispersion) is mixed with the pharmaceutical acceptable excipient in suitable proportions and compressed into the required shape and size. In some embodiments, when the composition is in the form of a capsule, the capsules of various types are known in the art. For example, capsules of hydroxypropyl methylcellulose or gelatin may be used.

The present disclosure can be further understood by the following non-limiting examples.

EXAMPLE 1

Preparation of [1-((11S)-7,8-difluoro(6H,11H-dibenzo[c,f]thiepin-11-yl))-4,6-dioxospiro[11,2,3,9-tetrahydropyridino[1,2-e]pyridazine-3,1'-cyclopropane]-5-yloxy]methyl methoxyformate (Compound A)

[1-((11S)-7,8-difluoro(6H,11H-dibenzo[c,f]thiepin-11-yl))-4,6-dioxospiro[1,2,3,9-tetrahydropyridino[1,2-e]pyridazine-3,1'-cyclopropane]-5-yloxy]methyl methoxyformate (Compound A) was prepared by the synthetic route and protocols reported in Hsu et al., WO2019/144089,or Chen et al., WO2021/239126. Shown below is the mass spectrum (MS) and nuclear magnetic resonance of Compound A: MS: m/z 541.0 (M$^+$+1); $^1$H NMR (CDCl$_3$) δ 7.31 (d, 1H), 7.06-7.00 (m, 4H), 6.85-6.84 (m, 1H), 6.73 (d, 1H), 6.03 (d, 1H), 5.96 (d, 1H), 5.80 (d, 1H), 5.49 (d, 1H), 5.15 (s, 1H), 4.13 (d, 1H), 4.05 (d, 1H), 3.87 (s, 3H), 2.91 (d, 1H), 1.95-1.90 (m, 1H), 1.49-1.48 (m, 1H), 0.88-0.76 (m, 2H).

EXAMPLE 2

Preparation of Amorphous Solid Dispersions

The amorphous solid dispersions of the present disclosure were prepared by spray drying well known in the art. For example, see Singh et al., Advanced Drug Delivery Reviews, 2016, 100, 27-50. Different pharmaceutically acceptable polymer, such as PVP-VA64, Soluplus, HPMCAS-MG, HPMCAS-HG, Eudragit® EPO, HPC-SSL, HPMCP HP-55, Kollidon SR, and PEG3350, were used for making the amorphous solid dispersions of this disclosure. Spray dryer 4M8-Trix was used to prepare the amorphous solid dispersions. The spray drying concentration of Compound A was set at 25 mg/mL. Compound A was mixed with different pharmaceutical acceptable polymers at various ratios and dissolved in the solvents, such as acetone, in glass bottles to provide a feeder solution. The obtained feeder solution was passed through a nozzle as a fine spray into a chamber where the solvent was evaporated quickly to generate particles containing Compound A and a corresponding polymer. The resulting spray dried powder was dried further to remove residual solvents in a static dryer.

EXAMPLE 3

Dissolution Assessments

An amount of Compound A (about 6 mg) and an amorphous solid dispersion (equivalent to around 6 mg Compound A) were weighed into separate 8 ml bottle, and 6 ml FaSSIF (Fasted state simulated intestinal fluid) was added (target concentration 1.0 mg/mL). The suspensions were stirred using a thermomixer at 37° C. under 600 rpm and 200 µL of suspensions were withdrawn at pre-set time intervals (such as 5 min) and then centrifuged at 14000 rpm for 4 min. Then, 100 µL of supernatant was diluted with 500 µL ACN (Acetonitrile) to prevent precipitation, and was analyzed by HPLC.

FaSSIF was prepared by following steps: 1) Place 0.1024 g sodium hydroxide, 0.7518 g sodium dihydrogen phosphate anhydrous and 1.5470 g sodium chloride in a 250 mL volumetric flask, add about 225 mL water, and adjust the pH to 6.5 with 1 N sodium hydroxide or 1N hydrochloric acid. Make up to volume (250 mL) with pure water. 2) Place and dissolve 0.4480 g SIF Powder Original with 100 mL of buffer (from step 1) in a 200 mL volumetric flask, add water to volume and mix well.

The solubility of Compound A and amorphous solid dispersions collected manually at 5 and 15 min in FaSSIF were listed in TABLE 1.

TABLE 1

Solubility of Compound A and amorphous solid dispersion (ASD) thereof

| Sample No. | Formulation | Drug | Polymer | Weight Ratio (Drug:Polymer) | Solubility (µg/mL) 5 min | 15 min |
|---|---|---|---|---|---|---|
| 1 | — | Compound A | — | — | 4.95 | 4.89 |
| 2 | ASD | Compound A | HPMCP HP-55 | 1:1 | 64.60 | 12.27 |
| 3 | ASD | Compound A | Kollidon SR | 1:1 | 16.65 | 12.46 |
| 4 | ASD | Compound A | PEG3350 | 1:1 | 6.63 | 6.51 |

TABLE 1-continued

Solubility of Compound A and amorphous solid dispersion (ASD) thereof

| Sample No. | Formulation | Drug | Polymer | Weight Ratio (Drug:Polymer) | Solubility (μg/mL) 5 min | 15 min |
|---|---|---|---|---|---|---|
| 5 | ASD | Compound A | PVP-VA64 | 1:1 | 115.30 | 10.82 |
| 6 | ASD | Compound A | Soluplus | 1:1 | 131.80 | 130.00 |
| 7 | ASD | Compound A | Soluplus | 1:1.5 | 128.20 | 135.10 |
| 8 | ASD | Compound A | Soluplus | 1:2 | 138.30 | 136.00 |
| 9 | ASD | Compound A | Eudragit ® EPO | 1:1 | 65.73 | 73.08 |
| 10 | ASD | Compound A | HPMCAS-MG | 1:1 | 130.90 | 133.40 |
| 11 | ASD | Compound A | HPMCAS-HG | 1:1 | 100.40 | 102.90 |
| 12 | ASD | Compound A | HPC-SSL | 1:1 | 112.80 | 119.10 |
| 13 | ASD | Compound A | HPC-SSL | 1:1.5 | 125.80 | 118.90 |
| 14 | ASD | Compound A | HPC-SSL | 1:3 | 140.00 | 75.9 |
| 15 | ASD | Compound A | HPC-SSL | 1:5 | 126.30 | — |

EXAMPLE 4

Stability Study of Amorphous Solid Dispersions

The amorphous solid dispersions were stored at 4° C. (closed), 20° C./60%RH (closed and open state) or 40° C./75%RH (closed and open state). After 10 days or 4 weeks, samples were observed by camera, characterized by XRPD and analyzed by HPLC for purity as well as kinetic solubility. All the samples for closed storage conditions were put into clear glass vials with gaskets and screwed caps. All the samples for open storage conditions were put into clear glass vials without cap, while the mouth of vials was covered by aluminium foil with pinholes to avoid cross-contamination.

Total impurity level (i.e. TRS%, total relative substances) of ASDs after stability tests were shown in TABLE 2. The sample number in TABLE 2 corresponds to the sample number in TABLE 1.

TABLE 2

| Sample No. | polymer | Initial TRS % | 4° C. Closed for 4 wks TRS % | 20° C./60% RH Closed for 4 wks TRS % | 20° C./60% RH Open for 4 wks TRS % | 40° C./75% RH Closed for 4 wks TRS % | 40° C./75% RH Open for 10 d #/ 4 wks TRS % |
|---|---|---|---|---|---|---|---|
| 2 | HPMCP HP-55 | 0.90 | — | — | — | 4.72 | 5.58 |
| 4 | PEG3350 | 0.82 | — | — | — | 0.86 | 0.82 |
| 5 | PVP-VA64 | 0.80 | 0.78 | — | — | — | 1.50 |
| 6 | Soluplus | 0.78 | 0.77 | 0.80 | — | 0.92 | 1.22 |
| 9 | Eudragit ® EPO | 0.91 | 1.46 | — | — | — | 45.31 # |
| 10 | HPMCAS-MG | 0.78 | 0.86 | 1.22 | — | 3.05 | 4.48 |
| 11 | HPMCAS-HG | 0.78 | — | 0.99 | 1.09 | 1.95 | 2.80 |
| 12 | HPC-SSL | 0.77 | 0.78 | — | — | — | 1.35 |

OTHER EMBODIMENTS

All of the features disclosed in this specification may be combined in any combination. Each feature disclosed in this specification may be replaced by an alternative feature serving the same, equivalent or similar purpose. Thus, unless otherwise stated, each feature disclosed is only an example of a series of equivalent or similar features. From the above description, one skilled in the art can easily ascertain the essential characteristics of the present disclosure.

The invention claimed is:

1. An amorphous solid dispersion comprising a compound of Formula (I) or a pharmaceutically acceptable salt thereof, and a pharmaceutically acceptable polymer;

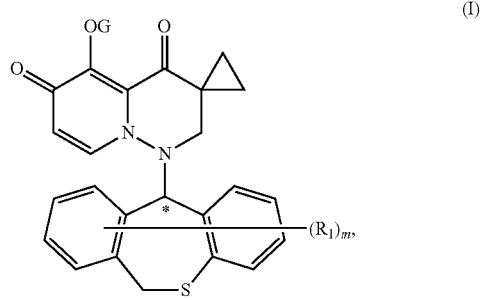

(I)

wherein
G is hydrogen or —C($R_2R_2'$)—O—C=O)—$R_3$, in which each of $R_2$ and $R_2'$ independently is hydrogen or $C_{1-4}$ alkyl; $R_3$ is $C_{1-4}$ alkyl;
$R_1$ is halogen, deuterium, or $C_{1-4}$ alkyl;
m is an integer of 1 to 9; and
the star (*) indicates a chiral center:,
wherein the pharmaceutically acceptable polymer is polyvinylpyrrolidone/vinyl acetate copolymer, polyvinyl caprolactam-polyvinyl acetate-polyethylene glycol graft copolymer, methacrylic acid and methyl methacrylate copolymer, hydroxypropyl cellulose (HPC), hydroxypropyl methyl cellulose acetate succinate (HPMCAS), hydroxypropyl methyl cellulose phthalate (HPMCP), Polyethylene glycol (PEG), or Kollidon SR; and wherein the weight ratio of the compound of Formula (I) or a pharmaceutically acceptable salt thereof to the pharmaceutically acceptable polymer is in a range between about 1:1 to about 1:5.

2. The amorphous solid dispersion according to claim 1, wherein the pharmaceutically acceptable polymer is polyvinyl caprolactam-polyvinyl acetate-polyethylene glycol graft copolymer, hydroxypropyl cellulose (HPC), or hydroxypropyl methyl cellulose acetate succinate (HPMCAS).

3. The amorphous solid dispersion according to claim 1, wherein the pharmaceutically acceptable polymer is polyvinyl caprolactam-polyvinyl acetate-polyethylene glycol graft copolymer, HPC-SSL, HPMCAS-MG, or HPMCAS-HG.

4. The amorphous solid dispersion according to claim 1, wherein the cyclic group in Formula (I) represented by the formula:

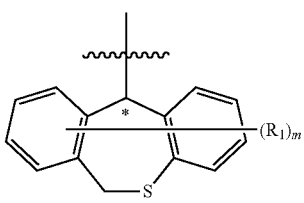

is a cyclic group represented by any one of the following structures:

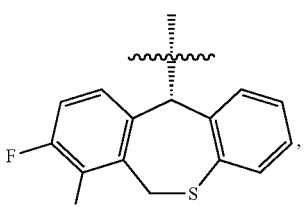

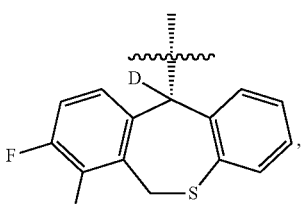

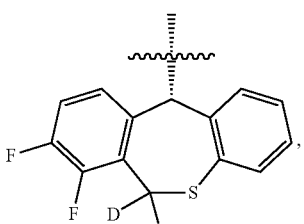

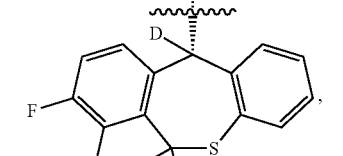

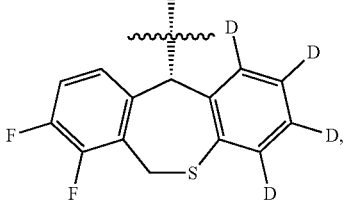

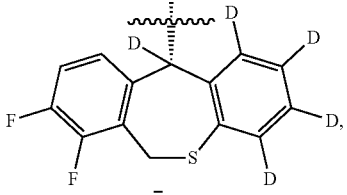

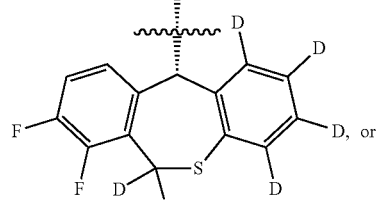

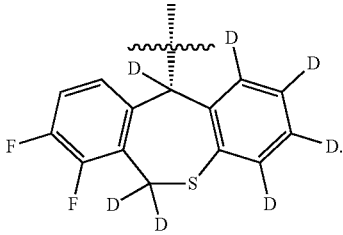

5. The amorphous solid dispersion according to claim 4, wherein the compound is [1-((11S)-7,8-difluoro(6H,11H-dibenzo[c,f]thiepin-11-yl))-4,6-dioxospiro[1,2,3,9-tetrahydropyridino[1,2-e[pyridazine-3,1'-cyclopropane[-5-yloxy [methyl methoxyformate or 1'-((11S)-7,8-difluoro-6,11-dihydrodibenzo [b,e]thiepin- 11-yl)- 1' ,2' -dihydro-5'-hydroxy-spiro[cyclopropane-1,3'-(3H)pyrido[1,2-b [pyridazine-4',6'-dione.

6. The amorphous solid dispersion according to claim 5, wherein the pharmaceutically acceptable polymer is polyvinyl caprolactam-polyvinyl acetate- polyethylene glycol graft copolymer, hydroxypropyl cellulose (HPC), or hydroxypropyl methyl cellulose acetate succinate (HPMCAS).

7. The amorphous solid dispersion according to claim 1, wherein the weight ratio of the compound of Formula (I) or a pharmaceutically acceptable salt thereof to the pharmaceutically acceptable polymer is in a range between about 1:1 to about 1:3.

8. The amorphous solid dispersion according to claim 1, wherein the pharmaceutically acceptable polymer is polyvinyl caprolactam-polyvinyl acetate-polyethylene glycol graft copolymer, hydroxypropyl cellulose (HPC), or hydroxypropyl methyl cellulose acetate succinate (HPMCAS).

9. The amorphous solid dispersion according to claim 1, wherein the compound of Formula (I) or a pharmaceutically acceptable salt thereof in the amorphous solid dispersion is 10-60% by weight.

10. The amorphous solid dispersion according to claim 9, wherein the compound of Formula (I) or a pharmaceutically acceptable salt thereof in the amorphous solid dispersion is 15-50% by weight.

11. The amorphous solid dispersion according to claim 9, wherein the pharmaceutically acceptable polymer is polyvinyl caprolactam-polyvinyl acetate-polyethylene glycol graft copolymer, hydroxypropyl cellulose (HPC), or hydroxypropyl methyl cellulose acetate succinate (HPMCAS).

12. A pharmaceutical composition comprising the amorphous solid dispersion according to claim 1 and one or more pharmaceutically acceptable excipients.

13. The pharmaceutical composition according to claim 12, wherein the pharmaceutically acceptable polymer is polyvinylpyrrolidone/vinyl acetate copolymer, polyvinyl caprolactam-polyvinyl acetate-polyethylene glycol graft copolymer, methacrylic acid and methyl methacrylate copolymer, hydroxypropyl cellulose (HPC), hydroxypropyl methyl cellulose acetate succinate (HPMCAS), hydroxypropyl methyl cellulose phthalate (HPMCP), Polyethylene glycol (PEG), or Kollidon SR.

14. The pharmaceutical composition according to claim 13, wherein the weight ratio of the compound of Formula (I) or a pharmaceutically acceptable salt thereof to the pharmaceutically acceptable polymer is in a range between about 1:1 to about 1:5.

15. The pharmaceutical composition according to claim 12, wherein the pharmaceutical composition is in a form of capsule, tablet, powder, pellet, pill, suspension, granule, or inhalant.

16. The pharmaceutical composition according to claim 12, wherein the pharmaceutically acceptable excipients is selected from binders, glidants, plasticizers, solubilizers, stabilizing agents, antioxidants, diluents, surfactants, disintegrants, lubrients, fillers, wetting agents, sweeteners, colorants, flavors and mixtures thereof.

* * * * *